United States Patent
Zhang et al.

(10) Patent No.: US 11,944,601 B2
(45) Date of Patent: Apr. 2, 2024

(54) APPLICATIONS OF ELLAGIC ACID IN PREPARATION OF IMMUNOMODULATORY MEDICINES FOR TREATMENT OF NEUROMYELITIS OPTICA OR IMMUNE REJECTION AFTER SKIN TRANSPLANTATION

(71) Applicant: SHAANXI NORMAL UNIVERSITY, Xi'an (CN)

(72) Inventors: Yuan Zhang, Xi'an (CN); Wenhui Qi, Xi'an (CN); Xing Li, Xi'an (CN); Bing Han, Xi'an (CN); Peixin Shen, Xi'an (CN)

(73) Assignee: SHAANXI NORMAL UNIVERSITY, Xi'an (CN)

( * ) Notice: Subject to any disclaimer, the term of this patent is extended or adjusted under 35 U.S.C. 154(b) by 0 days.

(21) Appl. No.: 17/679,113

(22) Filed: Feb. 24, 2022

(65) Prior Publication Data
US 2023/0263769 A1    Aug. 24, 2023

(51) Int. Cl.
*A61K 31/37*  (2006.01)
*A61P 37/02*  (2006.01)

(52) U.S. Cl.
CPC .............. *A61K 31/37* (2013.01); *A61P 37/02* (2018.01)

(58) Field of Classification Search
CPC ..................................................... A61K 31/37
See application file for complete search history.

(56) References Cited

PUBLICATIONS

Toney et al., Biomedicines (2021), 9(2), 192.*
Pascal O. Berberat et al., "Heme Oxygenase-1-generated Biliverdin Ameliorates Experimental Murine Colitis", Inflamm Bowel Dis, Apr. 2005, pp. 350-359, vol. 11, No. 4.

* cited by examiner

*Primary Examiner* — Paul V Ward
(74) *Attorney, Agent, or Firm* — Zhigang Ma

(57) ABSTRACT

An application of ellagic acid and a metabolic derivative urolithin compound thereof in preparation of an immunomodulatory medicine is provided. Classical animal models of autoimmunity and immunoregulation, such as experimental autoimmune encephalomyelitis, neuromyelitis optica mouse model, ulcerative colitis, and skin transplantation, are used as examples to conduct experiments from various aspects and perspectives, such as neurological function scores, histopathological changes of lesions, inflammatory factor expression, and pro-inflammatory cell numbers. The experiments demonstrate that ellagic acid and its metabolic derivatives significantly improved experimental autoimmune encephalomyelitis recovery and inhibited the infiltration of inflammatory cells into CNS, ameliorated experimental colitis severity and restored length of colon, reduced NMO-IgG-induced brain damage and prevented astrocyte loss and demyelination, as well as suppressed graft rejection and upregulated a proportion of regulatory T cells in order to enhance immune tolerance. Therefore, EA and its metabolic derivatives have high clinical application value and development prospect.

5 Claims, 11 Drawing Sheets

APPLICATIONS OF ELLAGIC ACID IN PREPARATION OF IMMUNOMODULATORY MEDICINES FOR TREATMENT OF NEUROMYELITIS OPTICA OR IMMUNE REJECTION AFTER SKIN TRANSPLANTATION

FIELD OF THE DISCLOSURE

The disclosure relates to the field of biomedical technologies, particularly to applications of ellagic acid and metabolic derivatives thereof in preparation of immunomodulatory medicines, and more particularly in the preparation of medicines for treating a variety of autoimmune diseases and immune rejection after organ transplantation.

BACKGROUND OF THE DISCLOSURE

Immunomodulators are a class of medicines that can regulate the function of the immune system by enhancing or inhibiting function of cells associated with the immune response (T lymphocytes, B lymphocytes, macrophages, etc.) to restore them to normal levels for therapeutic purposes. Immunomodulators are mainly used for organ transplantation anti-rejection and autoimmune diseases, such as rheumatoid arthritis (RA), systemic lupus erythematosus (SLE), vitiligo, psoriasis, inflammatory bowel disease (IBD), graft versus-host disease (GVHD), neuromyelitis optica (NMO) and multiple sclerosis (MS). Among them, MS is a chronic inflammatory demyelinating disease in which abnormally activated immune cells attack central nervous system (CNS). The disease is characterized by inflammatory cytokine infiltration and demyelination, and clinical symptoms mainly include neurological dysfunction, diplopia, limb sensory or activity disorder, ataxia and so on. The incidence rate of MS varies from region to region, and the pathogenesis is not fully understood. The current research indicates that it may be related to genetic factors, viral infection, environmental factors, autoimmunity and so on. Experimental autoimmune encephalomyelitis (EAE) has become the most widely used animal model because of its similar pathological characteristics and disease progression with MS. NMO is an acute or subacute demyelinating disease in which the optic nerve and spinal cord are involved simultaneously or successively. Its clinical feature is acute or subacute onset of monocular or binocular blindness, accompanied by transverse or ascending myelitis in the days or weeks before and after it. The etiology of the disease is still unclear. It is generally believed that aquaporin 4 (AQP4) antibodies enter the central nervous system through the blood-brain barrier, causing degradation of astrocyte foot processes by autoantibody immunoglobulin G (NMO-IgG) and complement, followed by activation of macrophages, eosinophils, and neutrophils, ultimately leading to damage to white matter and gray matter including axons and oligodendrocytes. Compared with MS, the astrocyte injury of NMO is significantly greater than that of myelin sheath and neurons. Autoimmune astrocytic lesions are the main pathological basis of NMO. Ulcerative colitis (UC), a type of IBD, is a chronic non-specific inflammatory disease that occurs in the colorectum, and the cause is not clear. The disease often occurs in young and middle-aged people. Its symptoms such as diarrhea, mucus and bloody purulent feces and abdominal pain seriously affect the quality of life of patients. Its etiology is complex, involving genetics, immunity, flora and other aspects. Because the disease is difficult to cure, easy to relapse, high risk of cancer, and often requires lifelong use of immunosuppressants, the World Health Organization lists it as one of the modern refractory diseases.

The biggest application market of immunomodulators is immune rejection after organ transplantation. According to the statistics of the National Health Commission of the People's Republic of China, about 300,000 people in China need transplantation every year due to end-stage organ failure. However, there are only about 10,000 organ transplantation operations every year, with a supply-demand ratio of 1:30, which is a huge gap. In such a serious shortage of donor organs, how to protect the function of transplanted organs after transplantation has become an urgent problem to be solved. Acute and chronic rejection after organ transplantation is the most common and critical clinical problem after organ transplantation, and is one of the important causes of loss of function of transplanted organs. Although first-line medicines such as cyclosporin A (CSA), fingolimod (FTY-720) and cyclophosphamide (CTX) have been developed in recent years, these medicines have certain limitations in application. For instance, fingolimod have few sources and high cost; cyclosporin and cyclophosphamide have extensive immunosuppressive effects, which are easy to cause various toxic and side effects and complications. The application of natural plant-derived anti-inflammatory medicines in immunoregulation has gradually attracted people's attention and achieved some results. For example, *Tripterygium* glycosides, the representative preparation of *Tripterygium wilfordii* Hook. F (TwHF), has been recognized by the World Health Organization (WHO) as "China's first new plant medicine preparation" for the treatment of arthritis. Due to the wide source of natural products and rich species diversity, it is a huge reserve of candidate medicines for immunomodulators.

Ellagic acid (EA) is a natural polyphenolic antioxidant widely distributed in many pulpy fruits and nuts such as pomegranate, strawberry, blackberry and walnut. It is a dimeric derivative of 3,4,5-trihydroxybenzoic acid (also referred to as gallic acid or gallnut acid) in the form of a trans-gallic acid tannin. Ellagitannin (ET) exists in nature mainly in condensed form. In vivo, ellagitannin is first hydrolyzed into ellagic acid, and ellagic acid is decomposed into urolithin substances that are easily absorbed and utilized through the biotransformation of intestinal flora, among which urolithin A (URA) is the most representative.

SUMMARY OF THE DISCLOSURE

The disclosure uses experimental autoimmune encephalomyelitis (EAE) model, neuromyelitis optica (WO) mouse model, ulcerative colitis (UC) model and skin transplantation model to prove the immunomodulatory effect of ellagic acid and its urolithin metabolic derivatives in autoimmune diseases and transplantation anti-rejection response.

The disclosure provides an application of ellagic acid and a metabolic derivative urolithin compound thereof in preparation of an immunomodulatory medicine.

In an embodiment, the ellagic acid and the metabolic derivative urolithin compound thereof are used in a preparation of a medicine for treating of a variety of autoimmune diseases and immune rejection after organ transplantation.

In an embodiment, a molecular formula of the ellagic acid is $C_{14}H_6O_8$, and a structural formula of the ellagic acid is as follows:

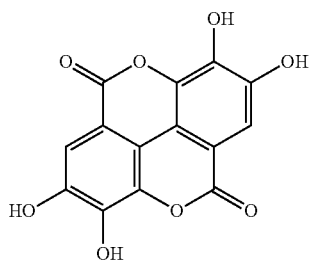 [SMILES: O=c1oc2c(O)c(O)cc3c(=O)oc4c(O)c(O)cc1c4c23]

The metabolic derivative urolithin compound of the ellagic acid is one selected from a group consisting of urolithin A, urolithin B, urolithin C and urolithin D, and structural formulas of the urolithin A, the urolithin B, the urolithin C and the urolithin D are respectively as follows:

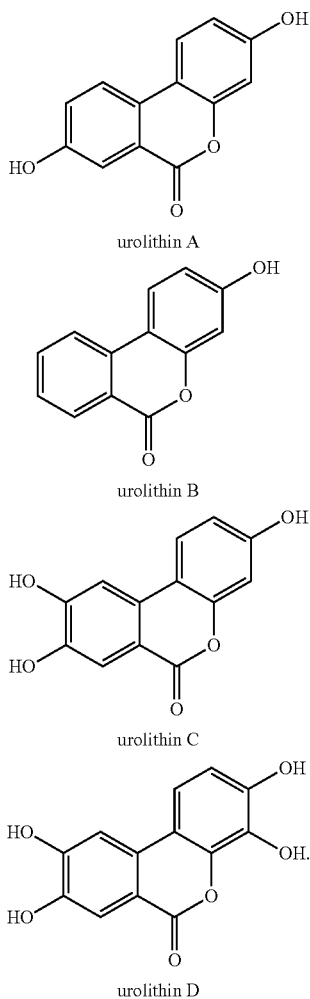

urolithin A urolithin B urolithin C urolithin D

The disclosure also provides an immunomodulatory medicine, of which the main active ingredients (also referred to as main effective component) include one or more of ellagic acid and its metabolic derivatives urolithin compounds.

The immunomodulatory medicine can be prepared into a pharmaceutically acceptable pharmaceutical preparation.

The pharmaceutical preparation as described above can be made into injections, nasal drops, eye drops, sprays, tablets, powders, granules, capsules, oral liquids, ointments and cream.

Compared with the prior technologies, the beneficial effects of the disclosure are as follows:

The disclosure through the whole animal model experiments proves that ellagic acid and its metabolic derivatives can effectively improve experimental autoimmune encephalomyelitis recovery and inhibit the infiltration of inflammatory cells into CNS, ameliorate the bloody feces symptoms of ulcerative colitis mice and restore length of colon, reduce NMO-IgG-induced brain damage and prevent astrocyte loss and demyelination, as well as prolong the survival time of skin grafts in skin transplantation and upregulate the proportion of regulatory T cells. Therefore, ellagic acid and its metabolic derivatives can be used to prepare immunomodulatory medicines.

DETAILED DESCRIPTION OF EMBODIMENTS

Figure 1A:
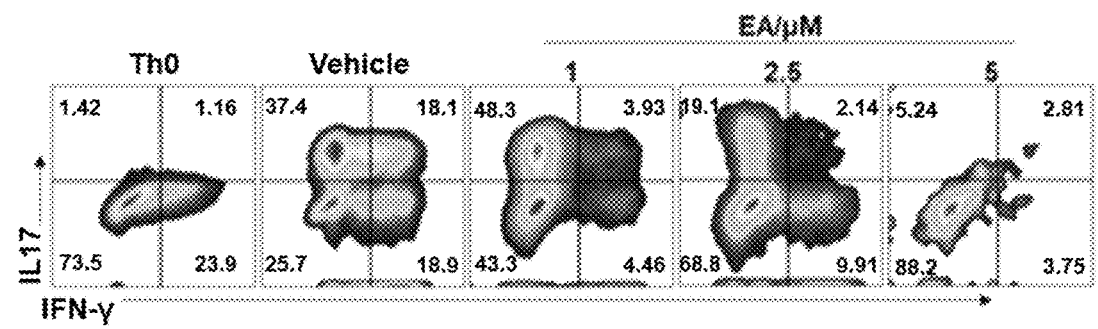
FIG. 1a shows effect of ellagic acid (EA) on T-helper 17 (Th17) cell polarization in embodiment 1 of the disclosure.

An application of ellagic acid and metabolic derivatives thereof in the preparation of immunomodulatory medicines is described in detail below in combination with the accompanying drawings and specific embodiments.

The disclosure provides the new application of ellagic acid and its metabolic derivative urolithin thereof in preparation of immunomodulatory medicines.

The application of ellagic acid and its metabolic derivatives provided by the disclosure includes two aspects:

1) An application of ellagic acid and urolithin metabolic derivatives thereof in inhibition of excessive immune response (i.e., autoimmune diseases);

2) An application of ellagic acid and urolithin metabolic derivatives thereof in the preparation of transplantation anti-rejection medicines.

Specifically:

Ellagic acid and its metabolic derivatives effectively inhibited clinical scores in EAE mice at prevention, initiation and peak. Histological evaluation of hematoxylin-eosin (H&E) staining and luxol fast blue (LFB) showed that the inflammatory cells, demyelinating degree and the number of inflammatory cells infiltrating in the central nervous system (CNS) of EAE mice treated with ellagic acid and its metabolic derivatives decreased significantly.

Ellagic acid and its metabolic derivatives significantly inhibited the loss of aquaporin 4 (AQP4) protein of astrocyte, astrocyte activation and demyelination of CNS in neuromyelitis optica (WO) mice.

Ellagic acid and its metabolic derivatives significantly improved weight loss, fecal viscosity, fecal occult blood and other pathological conditions caused by ulcerative colitis, and restored colon length of enteritis mice. They inhibited the infiltration of inflammatory cells in the skin transplantation model, increased the proportion of regulatory T cells in peripheral immune system, and enhanced immune tolerance.

The disclosure also provides an immunomodulatory medicine, of which the main active ingredients include one or more of ellagic acid and its metabolic derivatives urolithin compounds.

The immunomodulatory medicine can be introduced into the body such as muscle, intradermal, subcutaneous, venous and mucosal tissues through injection, spraying, nasal instillation, eye instillation, penetration, absorption, physical or chemical mediated methods. Alternatively, it is mixed or wrapped by other substances and introduced into the body.

One or more pharmaceutically acceptable carriers can also be added to the immunomodulatory medicine, such as diluents, excipients, fillers, binders, wetting agents, disintegrants, absorption enhancers, surfactants, adsorbent carriers, lubricants, etc., which are conventional in pharmaceutical field.

The above immunomodulatory medicines can be made in various forms such as injection, tablet, powder, granule, capsule, oral solution, ointment, and cream. The above various dosage forms of medicines can be prepared according to the conventional methods in the pharmaceutical field.

In order to make the purpose, technical solutions and advantages of the disclosure clearer, the disclosure is further described in detail in combination with the embodiments below.

Embodiment 1

Effects of ellagic acid (EA) and its representative metabolic derivative urolithin A (URA) on T-helper cell 17 (Th17) and Treg polarization in vitro.

1. Experimental Treatment

Single-cell suspension of spleen isolated from normal female C57BL/6 mice (aged 8-10 weeks) was co-cultured with anti-CD3 (0.5 μg/mL), anti-CD28 (1 μg/mL), TGF-β (2 ng/mL), IL-6 (20 ng/mL), IL-1 β (10 ng/mL), anti-IL-4 (10 μg/mL) and anti-IFN-γ (10 μg/mL) for 3 days to induce differentiation into Th17 cells. Cells were cultured with anti-CD3 (0.5 μg/mL), anti-CD28 (1 μg/mL), TGF-β (2 ng/mL) and IL-2 (10 ng/ml) for 3 days to induce differentiation into Treg cells. Cytokines were detected by flow cytometry.

Total RNA was extracted by using RNAprep Pure Cell/Tissue Kit (TIANGEN) and then reverse transcribed with Hiscript QRT Supermix (Vazyme) according to the manufacturer's instructions. mRNA expression was determined by real-time quantitative PCR using 2×ChamQ™ SYBR® qPCR Master Mix (Vazyme). Data was quantitatively analyzed on Roche Molecular Biochemicals Light Cycler Software Version 3.5. Mouse GAPDH gene was used as endogenous control for sample normalization.

Figure 1B:
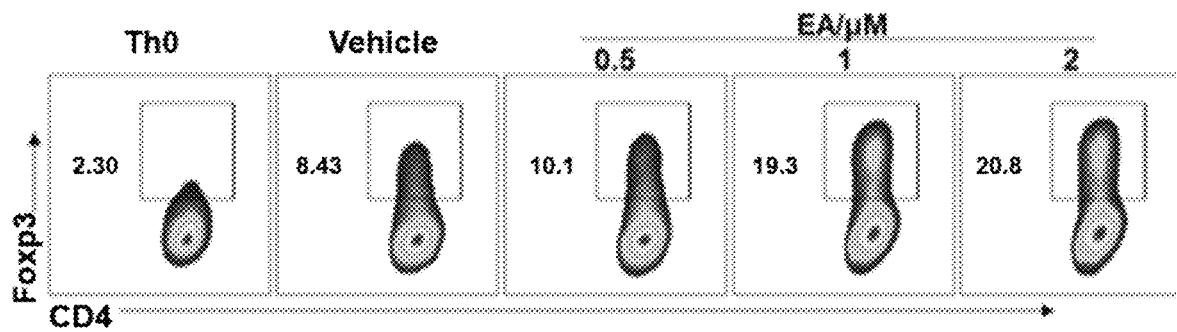
FIG. 1b shows effect of EA on Treg cell polarization in the embodiment 1 of the disclosure.
Figure 1C:
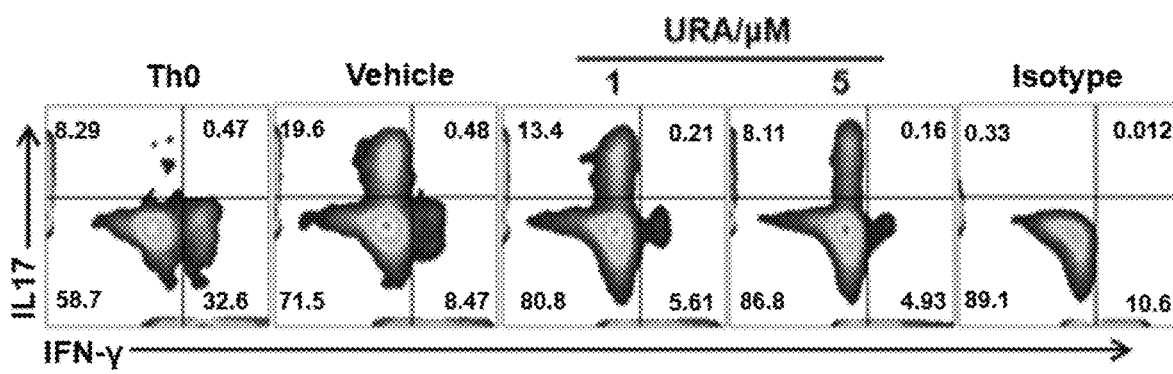
FIG. 1c shows effect of urolithin A (URA) on Th17 cell polarization in the embodiment 1 of the disclosure.

2. Experimental Results
   (1) As shown in FIG. 1a, the results of flow cytometry showed that EA at concentrations of 2.5 μM and 5 μM significantly inhibited the polarization of Th17 cells, and the inhibitory effect of 5 μM EA was better.
   (2) As shown in FIG. 1B, the results of flow cytometry showed that EA (0.5-2 μM) could promote the polarization of naïve CD4+T towards Treg in a dose-dependent manner.
   (3) As shown in FIG. 1c, the results of flow cytometry showed that URA at concentrations of 1 μM and 5 μM significantly inhibited Th1 and Th17 cells. 5 μM URA inhibited IL17 more significantly. There was no dose-dependent inhibition on IFN-γ.

Figure 1D:
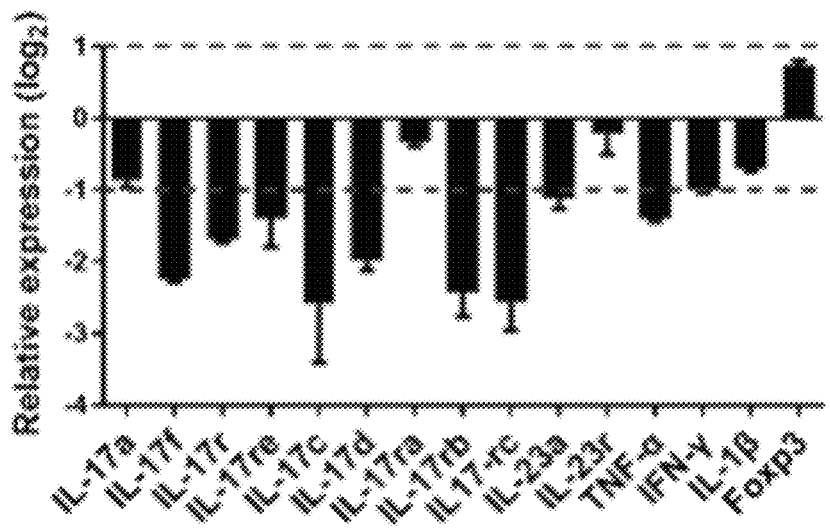
FIG. 1d shows effect of URA on expression levels of interleukin-17 (IL-17) family-related genes in CD4+ T cells in the embodiment 1 of the disclosure.

(4) As shown in FIG. 1d, RT-qPCR was performed on naïve CD4+ T cells treated with URA or phosphate-buffered saline (PBS) for 4 h under Th17 polarizing conditions. The results showed that URA treatment had a great influence on Th17-related genes, especially decreased the expression level of IL-17 family-related genes, and promoted the expression of Foxp3 to a certain extent.

T cells are important cell types that mediate autoimmune diseases and transplantation rejection, especially the balance between Th17 cells and Treg cells plays an extremely important role in experimental autoimmune encephalomyelitis (EAE), ulcerative colitis (UC) and post-transplantation immune rejection. Therefore, ellagic acid and its metabolic derivative urolithin compounds, which can regulate Th17 cells and Treg cells, can be used as immunomodulators to exert pharmacological effects in the above three diseases.

Embodiment 2

Ellagic acid and its metabolic derivative URA were administered at different stages to alleviate central inflammation in EAE mice.

1. Experimental Treatment

Female C57BL/6 mice aged 8-12 weeks were purchased from Air Force Military Medical University (Xi'an, China). Mice were fed under standard light and temperature conditions. All experimental procedures and protocols were approved by the institutional animal ethics Committee of Shaanxi Normal University and carried out in accordance with the approved institutional guidelines and regulations.

EAE mice were randomly divided into EA groups and URA groups. EA groups were divided into blank control group, fingolimod (FTY-720) positive control group (0.1 mg/kg) and EA administration group (0.1 mg/kg). URA groups were divided into blank control group and URA administration group (25 mg/kg). To induce EAE, mice were immunized at two sites on the back with 200 μg of myelin oligodendrocyte glycoprotein peptide 35-55 ($MOG_{35-55}$) (Genescript) in 200 μL of emulsion containing 50% complete Freund's adjuvant with 5 mg/ml *Mycobacterium tuberculosis* H37Ra (Difco). All mice were i.p. injected with 200 ng pertussis toxin (Sigma-Aldrich) in PBS on days 0 and 2 postimmunization (p.i.). Ellagic acid (EA) and its metabolic derivative URA were purchased from Ark Pharm, Inc and respectively administered to EAE mice on the day of immunization, the 11th day p.i and the 17th day p.i.

Two researchers evaluated clinical scores daily:

0: no clinical symptoms, 0.5: stiff tail, 1: lame tail, 1.5: reeling gait and tail tension, 2: limping tail and reeling gait (ataxia), 2.5: ataxia with local paralysis of limbs, 3: complete paralysis of one limb, 3.5: complete paralysis of a first limb and partial paralysis of a second limb, 4: complete paralysis of both limbs; 4.5: dying, 5: death.

Mice were sacrificed at day 20 p.i. Approximately 0.5 cm of the lumbosacral enlarged spinal cord was removed from the sacrificed mouse and fixed in 4% (w/v) paraformaldehyde. Sections were paraffin-embedded and stained with hematoxylin and eosin (H&E) and LFB, or stained with myelin basic protein (MBP) after frozen sections and finally observed by light microscopy (Nikon, Japan). The remaining brain and spinal cord tissues were mechanically shredded in petri dishes using a neural tissue dissociation kit (Miltenyi Biotec, 130-092-628). Preparation of solution I: enzyme P 50 μL+buffer X 1900 μL (per mouse) and solution II: enzyme A 10 μL+buffer Y 20 μL (per mouse). Tissues were repeatedly digested for isolating CNS mononuclear cells in a shaker at 37° C., 70 rpm for 15 min. The above dissociated cells were passed through a 70 μm nylon mesh and the filter was rinsed with PBS. After centrifugation at 300 g for 10 min, the resulting cell pellet was blown off, and subjected to gradient centrifugation with 70% and 30% percoll (GE Healthcare). Both the rate of increase and decrease were adjusted to 1. Then the dropper was inserted into the middle of the two liquid layers to slowly aspirate about 15 mL to obtain mononuclear cells (MNCs).

For flow cytometry surface marker staining, the cells were incubated with surface-stained fluorescent microsphere-coupled antibodies or isotype control antibodies on ice for 30 min. To analyze MOG-specific infiltrating inflammatory cells, CNS-infiltrating MNCs were stimulated with 10 μg/mL MOG for 24 h, followed by 50 ng/mL phorbol myristate acetate (PMA) and 500 ng/mL ionomycin for 5 hours in the presence of GolgiPlug. Then, the cells were washed, fixed and permeabilized with FIX&PERM solution (Invitrogen), and the intracellular factors were stained with corresponding internal staining antibodies. Data were further detected by flow cytometry and analyzed by Flowjo software (Treestar, Ashland, OR).

Figure 2A:
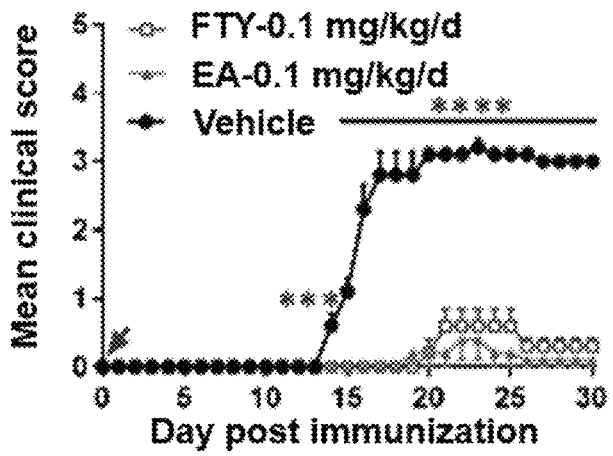
FIG. 2a is a clinical score diagram of experimental autoimmune encephalomyelitis (EAE) mice administered with medicines from day 0 of immunization in embodiment 2 of the disclosure.
Figure 2B:
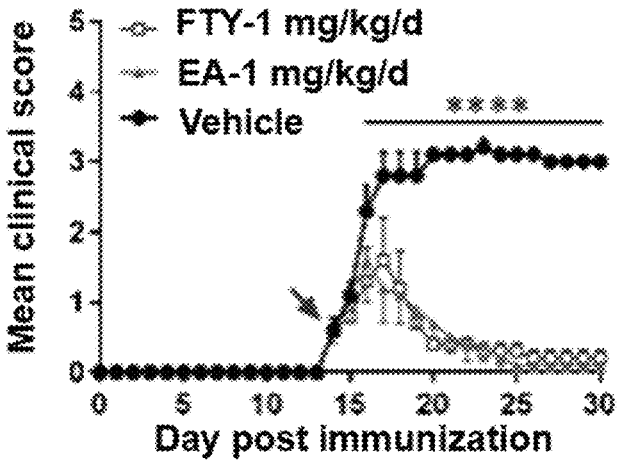
FIG. 2b is a clinical score diagram of EAE mice administered with medicines from the onset stage of the disease in the embodiment 2 of the disclosure.
Figure 2C:
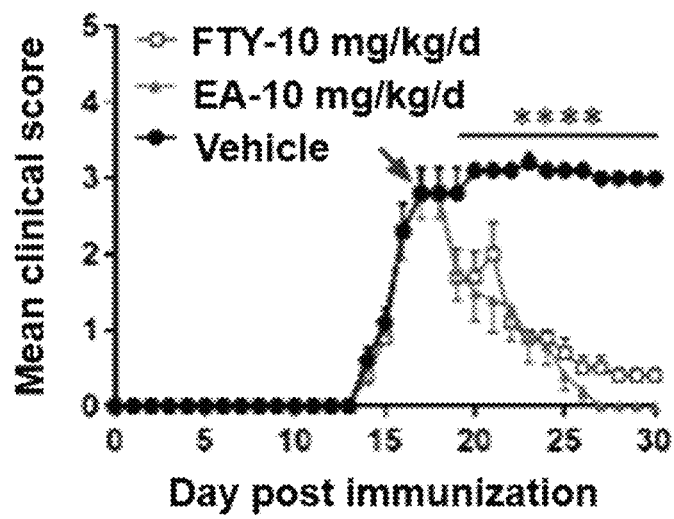
FIG. 2c is a clinical score diagram of EAE mice administered with medicines from the peak of the disease in the embodiment 2 of the disclosure.
Figure 2D:
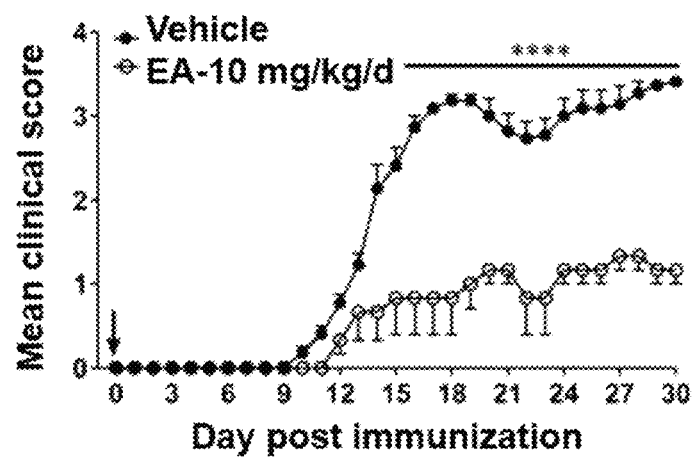
FIG. 2d is another clinical score diagram of EAE mice administered EA on day 0 of immunization in the embodiment 2 of the disclosure.

2. Experimental Results (1) EAE mice were randomly divided and were intraperitoneally injected with different doses of EA from the day of immunization, the onset stage of the disease (day 11 p.i.) and the peak period of the disease (day 17 p.i.). The results in FIGS. 2a-2c showed that EA not only inhibited the course of disease in the prevention stage, but also significantly inhibited the development of EAE during the onset and peak period of disease. Its therapeutic effect was equivalent to that of clinical immunomodulatory medicine fingolimod (FTY-720). EA oral administration can also effectively alleviate the progress of the disease, but the dosage is 250 times that of injection, because its effect needs to be transformed into metabolites such as URA through intestinal flora (FIG. 2d).

Figure 3A:
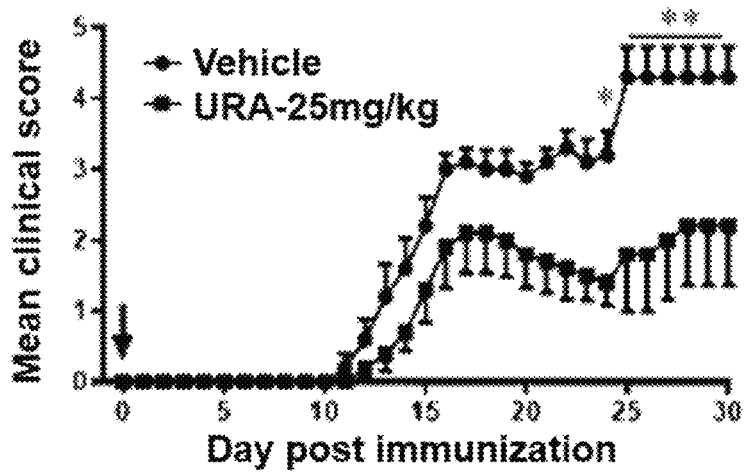
FIG. 3a shows a clinical scoring result of EAE mice administered with URA from day 0 of immunization in the embodiment 2 of the disclosure.
Figure 3B:
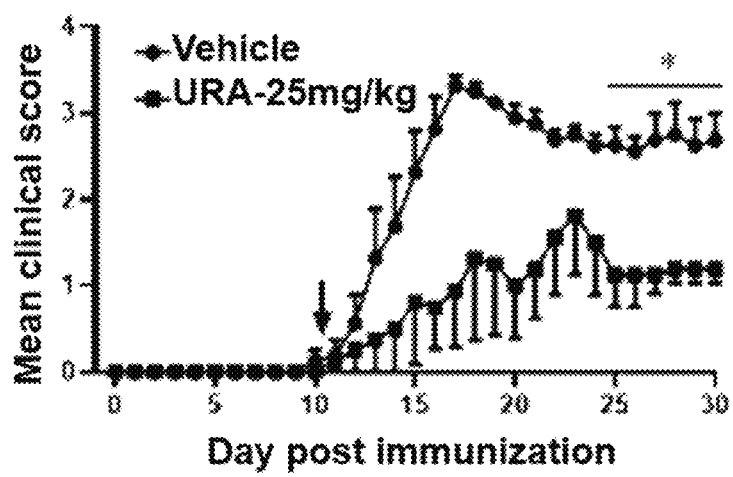
FIG. 3b shows a clinical scoring result of EAE mice administered with URA from the onset stage of the disease in the embodiment 2 of the disclosure.
Figure 3C:
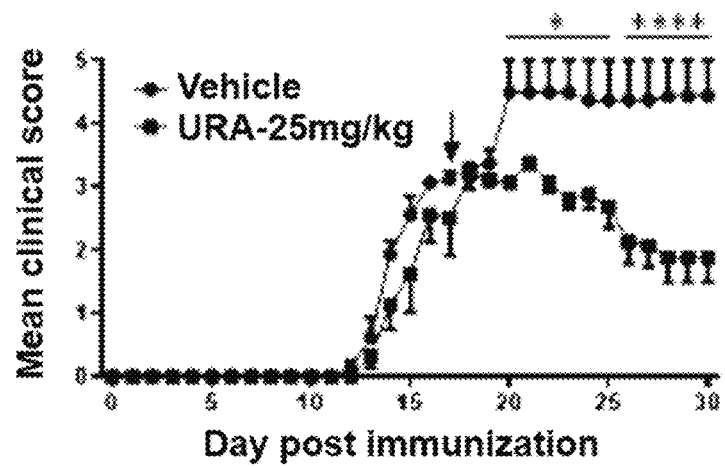
FIG. 3c shows a clinical scoring result of EAE mice administered with URA from the peak of the disease in the embodiment 2 of the disclosure.

(2) As shown in FIGS. 3a-3c, URA, the main metabolite of EA, also inhibited the condition of EAE and reduced the clinical scores of mice in the prevention stage (day 0 of p.i., FIG. 3a), onset stage (day 11 postimmunization, FIG. 3b) and peak period of disease (day 17 p.i., FIG. 3c).

Figure 4A:
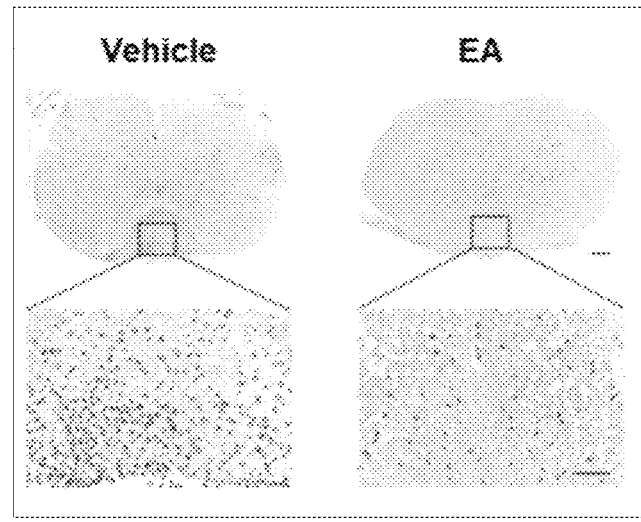
FIG. 4a shows a result of hematoxylin-eosin (H&E) staining of pathological sections of lumbosacral enlargement of spinal cord in the embodiment 2 of the disclosure.
Figure 4B:
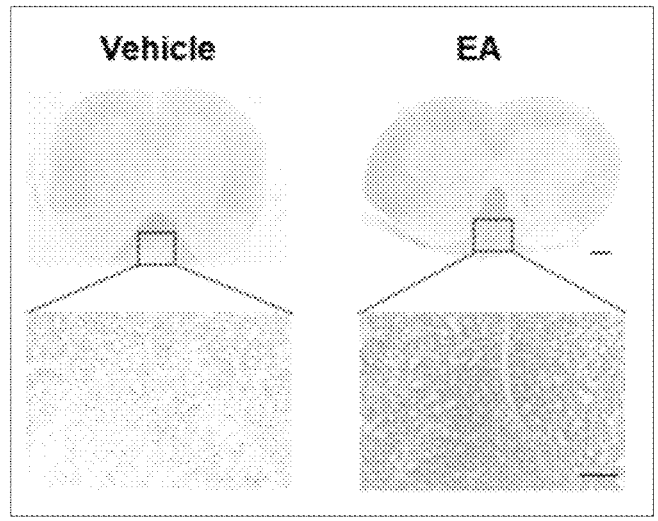
FIG. 4b shows a result of luxol fast blue (LFB) staining of pathological sections of lumbosacral enlargement of spinal cord in the embodiment 2 of the disclosure.
Figure 5A:
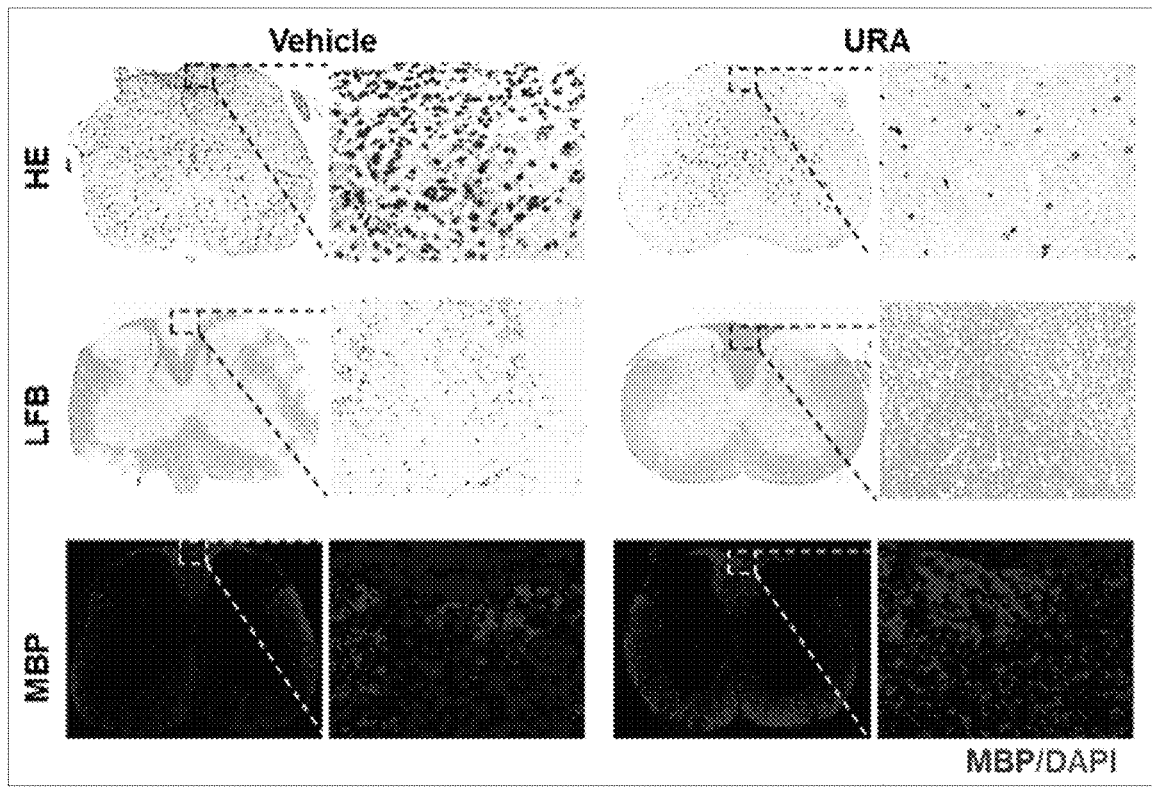
FIG. 5a shows results of H&E staining, LFB staining and myelin basic protein (MBP) staining of pathological sections of cervical enlargement of spinal cord in the embodiment 2 of the disclosure.
Figure 5B:
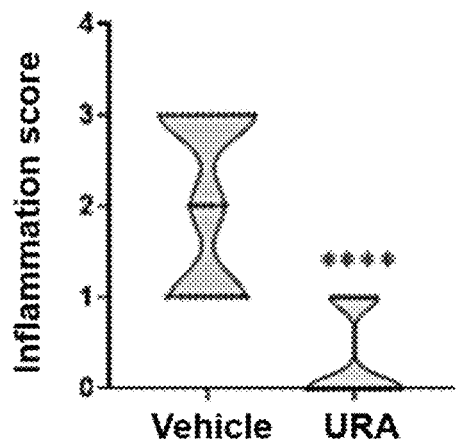
FIGS. 5b-5d show results of statistics of pathological sections of cervical enlargement of spinal cord in the embodiment 2 of the disclosure.
Figure 5C:
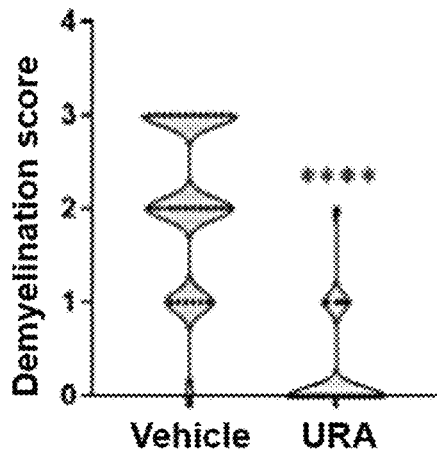
Figure 5D:
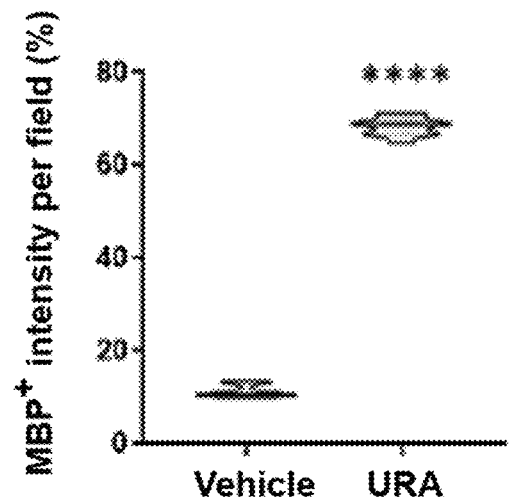

(3) As shown in FIGS. 4a-4b, the staining results of H&E (FIG. 4a) and LFB (FIG. 4b) showed that EA treatment significantly attenuated the infiltration of spinal cord inflammatory cells and demyelination of white matter.

(4) As shown in FIGS. 5a-5d, inflammatory cell infiltration and demyelination in the white matter of the spinal cord in URA treatment group were significantly relieved. In addition, the expression of MBP reflects the degree of myelin sheath integrity. The proportion of intact myelin sheath in the spinal cord of URA-treated mice was significantly increased compared with control mice.

Figure 6A:
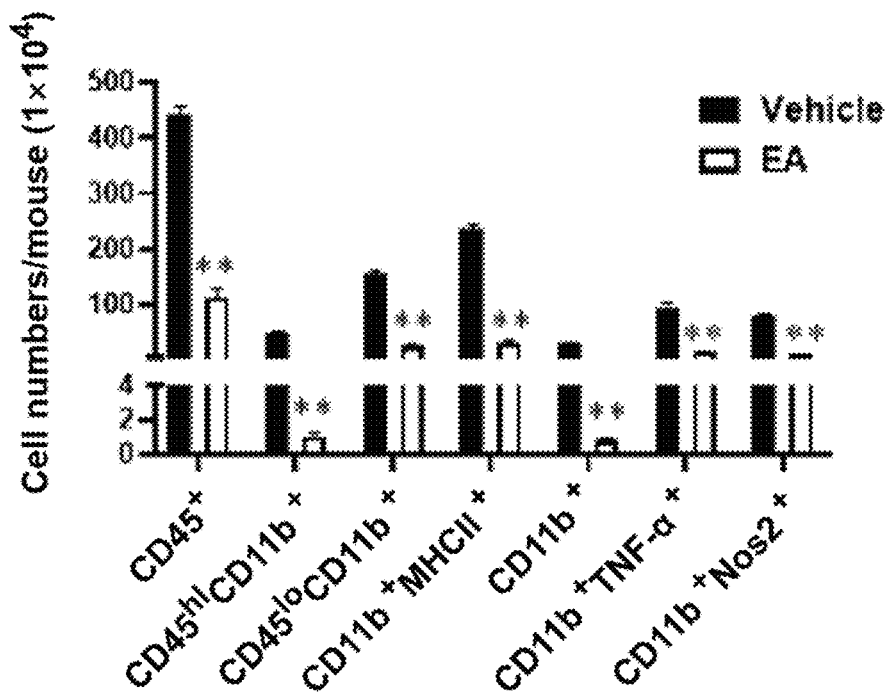
FIGS. 6a-6b show diagrams of absolute number of macrophages, activated M1 microglia and pathogenic T cells infiltrating into CNS in different treatment groups in the embodiment 2 of the disclosure.
Figure 6B:
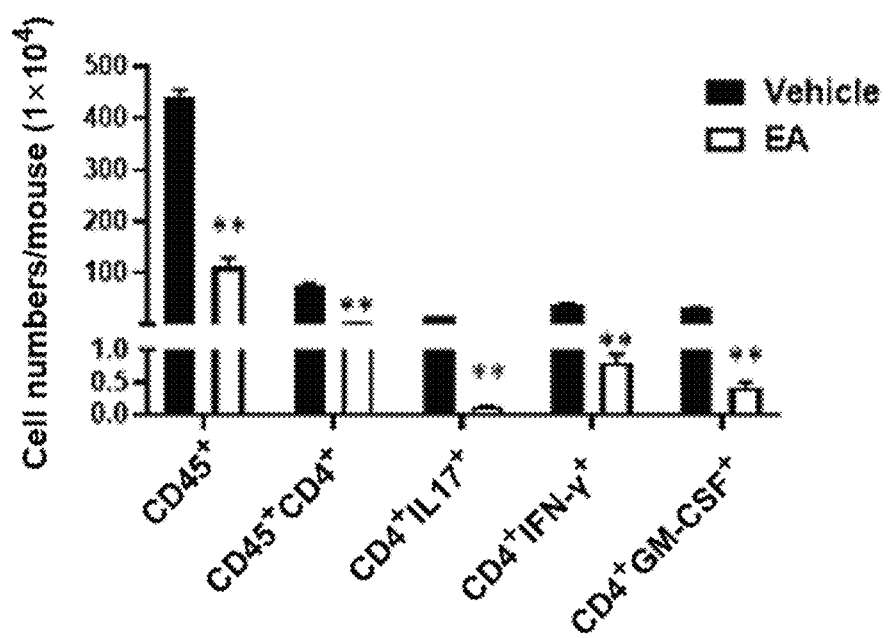

(5) As shown in FIGS. 6a-6b, after EA treatment, the absolute number of pro-inflammatory microglia and macrophages infiltrating into CNS decreased, specifically manifested as decreased absolute number of $CD45^{high+}CD11b^+$ (infiltrating macrophages, activated microglia), $CD45^{low+}CD11b^+$ (microglia), $CD11b^+$ MHC II$^+$, $CD11b^+TNF$-$\alpha^+$ and $CD11b^+$ Nos2$^+$ M1 microglia cells (FIG. 6a), which proved that EA inhibited the activation of inherent microglia in CNS during EAE disease progression. In addition, the absolute number of CD45+ (leukocytes), CD45+ CD4+ (T-helper cells), CD4+IL-17+, CD4+IFN-γ+, and CD4+GM-CSF+ cells infiltrating into the CNS was also significantly reduced under EA treatment (FIG. 6b).

In the embodiment 1, it was proved that EA and its metabolic derivative URA inhibited Th17 polarization and promote Treg polarization in vitro. Since the balance between Th17 and Treg is an important common feature in EAE, UC and transplantation rejection models, and EA and URA in the embodiment 2 significantly inhibited the pathological process of EAE, the embodiments of UC, transplantation rejection and NMO models no longer demonstrated the metabolites of EA one by one, but take EA as the representative.

Embodiment 3

Figure 7:
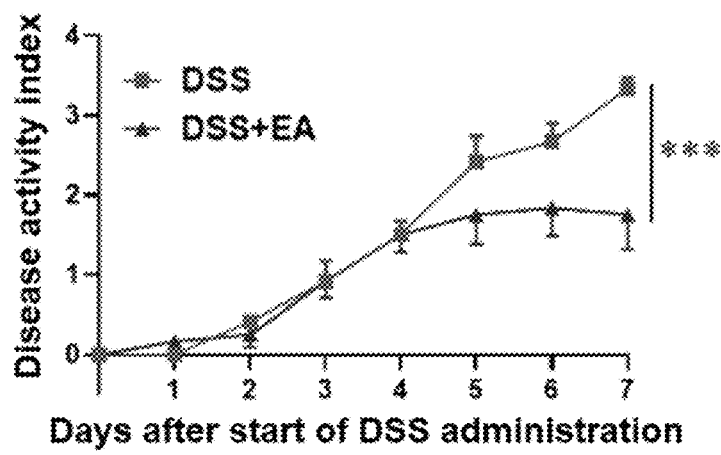
FIG. 7 shows a result of disease activity index scores of colitis mice in different treatment groups in embodiment 3 of the disclosure.
Figure 8:
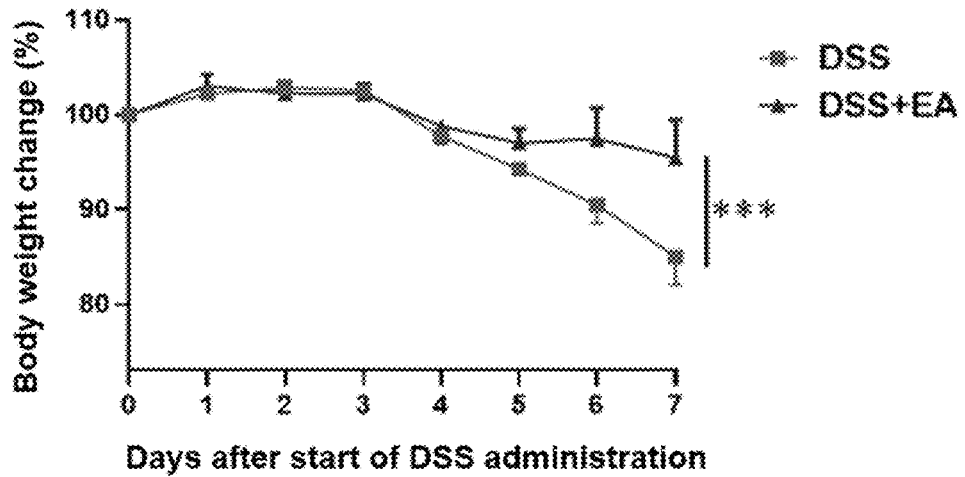
FIG. 8 shows percentage of body weight of colitis mice relative to that of pre-modeling in the embodiment 3 of the disclosure.
Figure 9A:
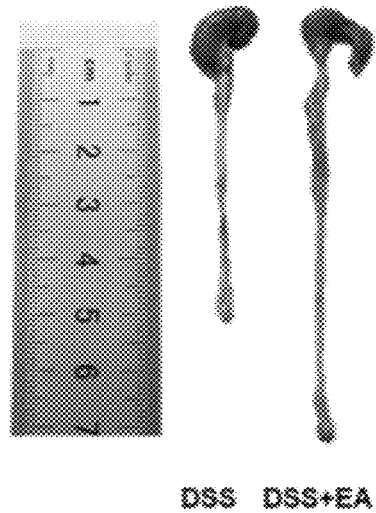
FIG. 9a shows measurements of colon length of colitis mice in the embodiment 3 of the disclosure.
Figure 9B:
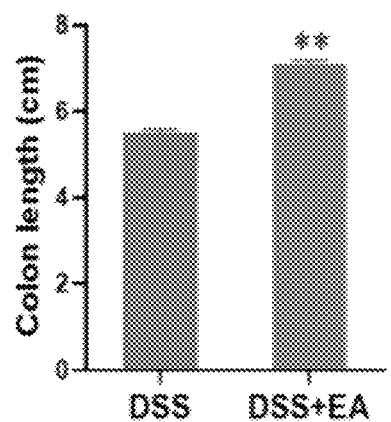
FIG. 9b shows a result of statistics of colon length of colitis mice in the embodiment 3 of the disclosure.

Ellagic acid alleviated inflammatory response and restored colon length in colitis mice.
  1. Experimental Treatment
  The mice were randomly divided into control group and EA treatment group. 2.5% (w/v) of dextran sodium sulfate (DSS) was added to drinking water continuously for 7 days to induce acute colitis, and mice in the treatment group were fed 100 mg/kg/d EA. During the experiment, mice were weighed regularly every day and the percentage change was calculated. In addition, the feces characteristics of mice were observed every day and divided into three grades according to the methods of Berberat et al. 1: normal, 2: increased stool viscosity and easily dispersed, 3: watery diarrhea. Moreover, hidden blood of mouse feces was measured by pyramidon method. If the mouse feces contained reddish-brown or bright red blood visible to the naked eye, it was determined as fecal blood. Finally, the disease activity index (DAI) of mice was calculated according to the scoring criteria of Berberat et al. The whole segment of colon from anus to the end of cecum of mice was taken, the length was measured and photographed for recording.
  2. Experimental Results
  (1) As shown in FIG. 7, the DAI score of EA treatment group decreased significantly compared with DSS control group.
  (2) As shown in FIG. 8, the percentage of weight loss in the EA treatment group was significantly lower than that in the DSS control group.
  (3) As shown in FIGS. 9a-9b, the length of the whole segment of the colon was measured. The results showed that the colon length was significantly restored in the EA treatment group.

Embodiment 4

Figure 10:
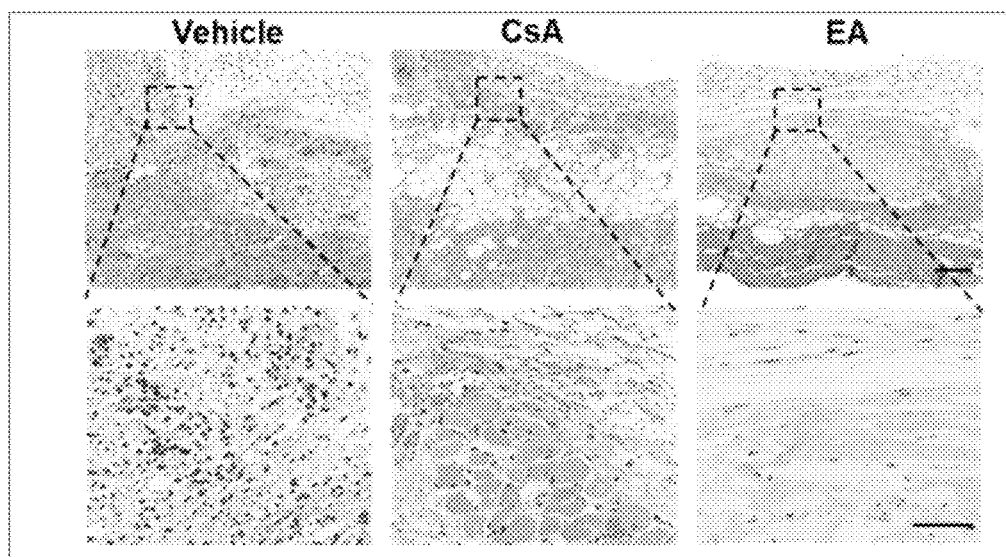
FIG. 10 shows a result of H&E staining of skin grafts in different treatment groups in embodiment 4 of the disclosure.
Figure 11:
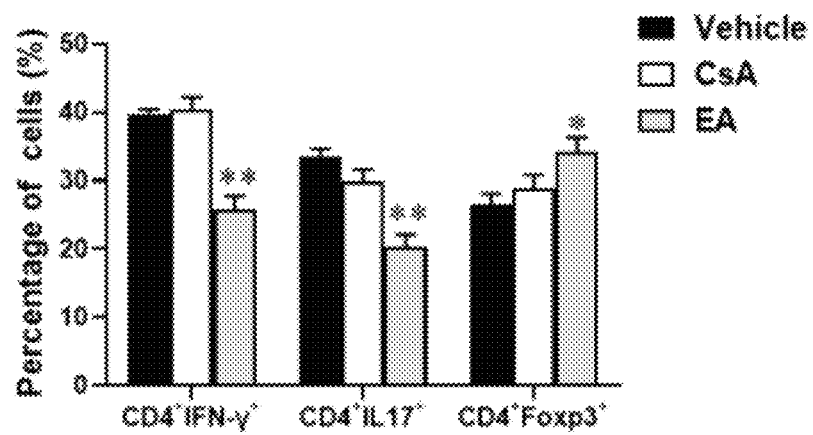
FIG. 11 shows proportions of Th1, Th17 and Treg cells in the peripheral immune system detected by flow cytometry in the embodiment 4 of the disclosure.
Figure 12:
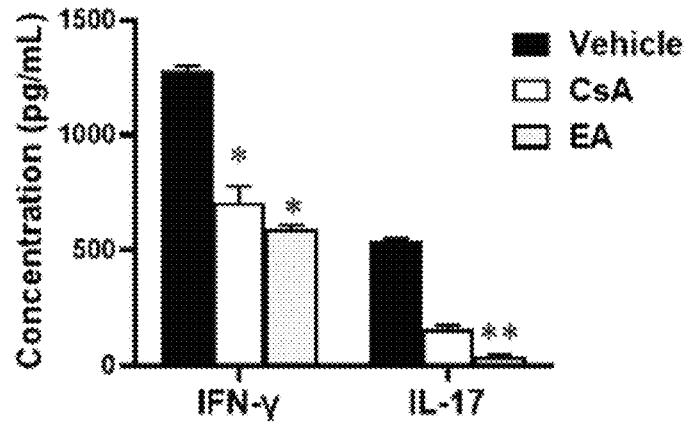
FIG. 12 shows contents of IFN-γ and IL-17 in the culture supernatant of spleen cells by enzyme linked immunosorbent assay (ELISA) in the embodiment 4 of the disclosure.

Ellagic acid reduced rejection and induced immune tolerance in skin transplantation model.
  1. Experimental Treatment
  The donor BALB/c mice were sacrificed, the dorsal hair was removed with a shaver. Appropriately sized skin grafts were cut, peeled off, washed, immersed in sterilized saline containing antibiotics for 5 minutes, and finally stored on ice for backup. The receptor C57BL/6 mice were intraperitoneally injected with 0.5% of pentobarbital sodium injection according to the body weight of 0.15 mL/20 g. After the mice were anesthetized, they were fixed on a surgical plate, the mid-dorsal parts of the mice body slightly to the lefts were selected as operation areas. Mice were shaved and disinfected with 75% alcohol to prepare graft beds. The prepared donor skin sheet was placed on the predetermined transplantation bed of recipient mice and then flattened. The skin patch was sutured to the transplant bed by discontinuous suture with 6-0 sutures. The recipient mice were administered therapeutic medicines from the day of surgery. Mice were observed for 7 consecutive days for inflammation, edema, necrosis, scab formation and shedding of the transplanted skin grafts on the back, and more than 80% necrosis of the skin grafts could be considered as complete rejection. The spleens of the receptor mice were taken on the 7th day to isolate single cells for flow cytometer detection. The supernatant of splenocytes was collected for enzyme-linked immunosorbent assay (ELISA).
  2. Experimental Results
  (1) As shown in FIG. 10, both EA and positive control medicine cyclosporin A (CsA) significantly inhibited the infiltration of inflammatory cells in the grafted skin.
  (2) After the single cells isolated from the spleen of receptor mice were cultured for 72 hours, flow cytometry was used for detection, and the results are shown in FIG. 11. The results showed that EA treatment significantly inhibited Th1 and Th17 inflammatory cells and increased the proportion of anti-inflammatory cell Treg, suggesting that EA induced immune tolerance.
  (3) As shown in FIG. 12, ELISA was used to detect the supernatant of splenocytes, the results showed the content of IFN-γ and IL-17 in EA treatment group was significantly reduced, and the effect was better than that of CsA.

Embodiment 5

Figure 13A:
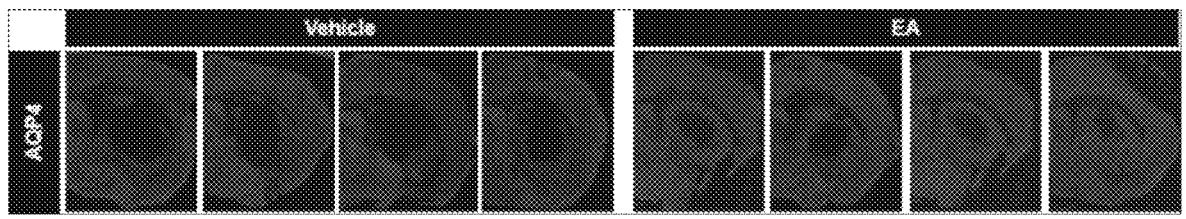
FIG. 13a shows a result of aquaporin 4 (AQP4) staining of brain slices in embodiment 5 of the disclosure.
Figure 13B:
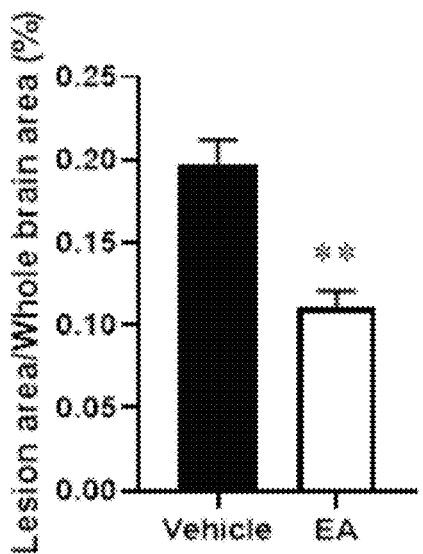
FIG. 13b shows a result of statistics of brain slices in the embodiment 5 of the disclosure.
Figure 14A:
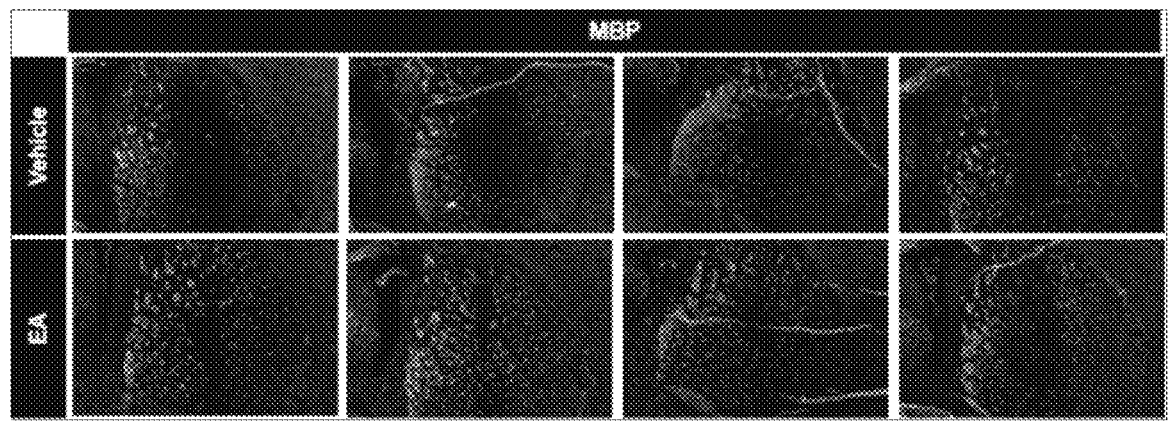
FIG. 14a shows a result of MBP staining of brain slices in the embodiment 5 of the disclosure.
Figure 14B:
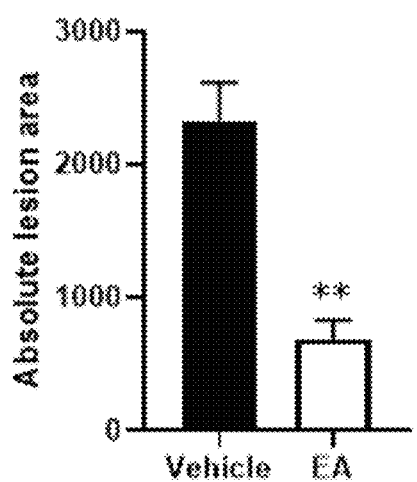
FIG. 14b shows a result of statistics of brain slices in the embodiment 5 of the disclosure.

Ellagic acid was used as a prophylactic to reduce neuromyelitis optica immunoglobulin G (NMO-IgG) induced cerebral lesion in mice.
  1. Experimental Treatment
  Female C57BL/6 mice aged 6-8 weeks were purchased from Air Force Military Medical University (Xi'an, China). Mice were fed under standard light and temperature conditions. All experimental procedures and protocols were approved by the institutional animal ethics Committee of Shaanxi Normal University and carried out in accordance with the approved institutional guidelines and regulations.
  WO mice were randomly divided into control group and EA group. In order to induce WO, mice were first anesthetized with 10% (w/v) of chloral hydrate and installed on a brain stereotactic apparatus (RWD Life Science), then the mouse scalp was cut along the midline, a small hole with a diameter of 1 mm was drilled on the skull 2 mm on the right side of the anterior fontanelle, and finally 5 μL microinjector (Hamilton) was inserted 3 mm deep and 2 μL of NMO-IgG and 3 μL of complement were injected at a rate of 1 μL/min. EA (2 mg/kg/d) and control solvents were administered to WO mice three days before surgery.
  The mice were sacrificed on the fifth day of modeling. The brain tissue was removed from the mice and fixed in 4% (w/v) of paraformaldehyde. The frozen sections were stained with AQP4 and MBP.
  2. Experimental Results
  (1) As shown in FIGS. 13a-13b, the AQP4 protein loss rate in EA group was lower than that in control group.
  (2) As shown in FIGS. 14a-14b, the degree of demyelination decreased after EA treatment.

The above disclosure is only specific embodiments of the disclosure, but embodiments of the disclosure are not limited to these illustrated embodiments. Any changes that can be thought of by those skilled in the field should fall into the protection scope of the disclosure.

What is claimed is:

1. An application method of ellagic acid comprising:
administering a medicine with the ellagic acid to a patient with neuromyelitis optica or immune rejection after skin transplantation;
wherein a molecular formula of the ellagic acid is $C_{14}H_6O_8$, and a structural formula of the ellagic acid is as follows:

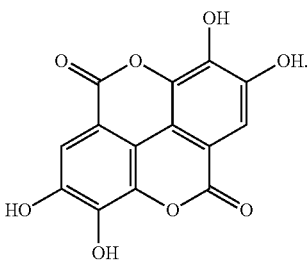

2. The application method according to claim 1, wherein the step of administering a medicine with the ellagic acid to a patient with neuromyelitis optica or immune rejection after skin transplantation comprises:
administering the medicine with a concentration of 2 milligrams per kilogram (mg/kg) of the ellagic acid per day within a treatment period to the patient with the neuromyelitis optica.

3. The application method according to claim 2, wherein the medicine is introduced into a body of the patient with the neuromyelitis optica or the immune rejection after skin transplantation through oral administration, injection, spraying, nasal instillation, eye instillation, penetration, absorption, and physical or chemical mediated method.

4. The application method according to claim 1, wherein before the step of administering a medicine with the ellagic acid to a patient with neuromyelitis optica or immune rejection after skin transplantation, the application method further comprises:
applying the ellagic acid to prepare the medicine; wherein the medicine is prepared into a pharmaceutically acceptable pharmaceutical preparation.

5. The application method according to claim 4, wherein the pharmaceutical preparation is one selected from a group consisting of injections, nasal drops, eye drops, sprays, tablets, powders, granules, capsules, oral liquids, ointments and creams.

* * * * *